United States Patent [19]

Clinton, deceased et al.

[11] Patent Number: 4,764,534

[45] Date of Patent: Aug. 16, 1988

[54] ANTICOCCIDIAL NAPHTHALENAMINES AND COMBINATIONS THEREOF

[75] Inventors: Albert J. Clinton, deceased, late of Indianapolis, American Fletcher National Bank and Trust Company, administrator; George O. P. O'Doherty, Greenfield, both of Ind.

[73] Assignee: Eli Lilly and Company, Indianapolis, Ind.

[21] Appl. No.: 631,665

[22] Filed: Jul. 17, 1984

Related U.S. Application Data

[63] Continuation of Ser. No. 374,801, May 4, 1982, abandoned.

[51] Int. Cl.⁴ .......................................... A61K 31/135
[52] U.S. Cl. ................................... 514/657; 514/555; 514/658; 564/429; 564/431
[58] Field of Search ................ 564/429, 431; 514/555, 514/657, 658

[56] References Cited

U.S. PATENT DOCUMENTS

| 2,212,825 | 8/1940 | Daudt et al. | 260/571 |
| 4,183,949 | 1/1980 | Hamprecht et al. | 424/304 |
| 4,311,710 | 1/1982 | Clinton et al. | 424/330 |
| 4,423,065 | 12/1983 | Clinton et al. | 424/304 |

FOREIGN PATENT DOCUMENTS

1383523  2/1975  United Kingdom .

OTHER PUBLICATIONS

U.S. Ser. No. 304403, filed Sep. 21, 1981, Clinton et al.

*Primary Examiner*—Robert V. Hines
*Attorney, Agent, or Firm*—Joseph A. Jones; Leroy Whitaker

[57] ABSTRACT

4-Substituted-N-[2,4-dinitro-6-(trifluoromethyl)-phenyl]-1-naphthalenamine derivatives, useful as anticoccidial agents both alone and in combination with polyether antibiotics.

26 Claims, No Drawings

ANTICOCCIDIAL NAPHTHALENAMINES AND COMBINATIONS THEREOF

This application is a continuation of Ser. No. 374,801, filed May 4, 1982, and now abandoned.

SUMMARY OF THE INVENTION

The present invention relates to novel naphthalenamine derivatives both alone and in combination with polyether antibiotics that are useful in controlling coccidiosis in animals. The present invention also provides compositions containing such compounds and combinations, as well as methods for their use.

DETAILED DESCRIPTION OF THE INVENTION

The present invention relates to a compound of the formula

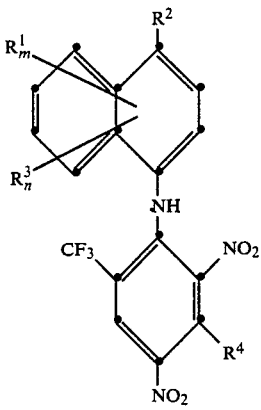

wherein:
$R^1$ is $C_1$–$C_4$ alkyl;
$R^2$ is halogen, $C_1$–$C_4$ fluoroalkyl, $C_1$–$C_4$ fluoroalkoxy or $C_1$–$C_4$ fluoroalkylthio;
$R^3$ is halogen;
$R^4$ is hydrogen or halogen;
m is 0, 1 or 2; and
n is 0 or 1;
with the proviso that when an $R^3$ substituent exists it is at other than the 2-position.

Preferred compounds of the present invention have the above formula wherein m and n are 0, $R^4$ is hydrogen and $R^2$ is as defined above.

The present invention also provides a method for controlling coccidiosis in animals which comprises administering to an animal a compound of the invention. A preferred method according to this invention is a method for controlling coccidiosis in poultry which comprises orally administering to the poultry a compound of the invention.

An additional embodiment of the invention is a composition comprising a compound of the above formula admixed with a suitable carrier. A preferred formula is a poultry feedstuff or premix composition comprising a compound of the invention and a suitable carrier.

The compounds of the present invention are preferably used in combination with a polyether antibiotic. It is therefore yet another object of the present invention to provide an anticoccidial combination, a method for controlling coccidiosis in animals employing such a combination, as well as compositions containing such a combination.

In the above formula, $C_1$–$C_4$ alkyl includes methyl, ethyl, n-propyl, isopropyl, n-butyl, sec.-butyl, isobutyl, t-butyl, and the like.

The term "halogen" represents fluorine, chlorine, bromine and iodine.

$C_1$–$C_4$ Fluoroalkyl is a $C_1$–$C_4$ alkyl group bearing one or more fluorine atoms. Such fluoroalkyl groups include trifluoromethyl, 1,1,2,2-tetrafluoroethyl, pentafluoroethyl, 1,2,3,3-tetrafluoropropyl, nonafluorobutyl, and the like.

$C_1$–$C_4$ Fluoroalkoxy is a $C_1$–$C_4$ alkoxy group bearing one or more fluorine atoms. Such fluoroalkoxy groups include difluoromethoxy, trifluoromethoxy, 1-fluoroethoxy, 1,1,2,2-tetrafluoroethoxy, pentafluoroethoxy, 1,2,2,3,3-pentafluoropropoxy, heptafluoropropoxy, 4,4,4-trifluorobutoxy, and the like.

$C_1$–$C_4$ Fluoroalkylthio is a $C_1$–$C_4$ alkylthio group bearing one or more fluorine atoms. Such fluoroalkylthio groups include trifluoromethylthio, 1,1,2,2-tetrafluoroethylthio, pentafluoroethylthio, 4,4,4-trifluorobutylthio, and the like.

The compounds listed below are typical of the compounds of the present invention. It will be understood that the compounds specifically named herein do not bound the scope of compounds provided by the invention, but are presented merely to assure that chemists will fully understand this invention.

4-Fluoro-N-[2,4-dinitro-6-(trifluoromethyl)phenyl]-1-naphthalenamine

4-Iodo-N-[2,4-dinitro-6-(trifluoromethyl)phenyl]-1-naphthalenamine

4-Trifluoromethyl-N-[2,4-dinitro-6-(trifluoromethyl)phenyl]-1-naphthalenamine

4-Pentafluoroethyl-N-[2,4-dinitro-6-(trifluoromethyl)phenyl]-1-naphthalenamine 6,7-Dimethyl-4-(1,1,2,2-tetrafluoroethoxy)-N-[2,4-dinitro-6-(trifluoromethyl)phenyl]-1-naphthalenamine 2-Isopropyl-4-chloro-N-[3-chloro-2,4-dinitro-6-(trifluoromethyl)phenyl]-1-naphthalenamine 8-n-Butyl-4-(4,4,4-trifluorobutoxy)-N-[3-bromo-2,4-dinitro-6-(trifluoromethyl)phenyl]-1-naphthalenamine 3-Methyl-6-propyl-4-heptafluoropropyl-N-[2,4-dinitro-6-(trifluoromethyl)phenyl]-1-naphthalenamine 3,4-Dichloro-N-[2,4-dinitro-6-(trifluoromethyl)phenyl]-1-naphthalenamine 4-(1,1-Difluoroethoxy)-N-[2,4-dinitro-6-(trifluoromethyl)phenyl]-1-naphthalenamine 4-(1,1,2,2-Tetrafluoroethoxy)-N-[2,4-dinitro-6-(trifluoromethyl)phenyl]-1-naphthalenamine 4-(1,1,2,2-Tetrafluoroethylthio)-N-[2,4-dinitro-6-(trifluoromethyl)phenyl]-1-naphthalenamine The compounds of the present invention may be conveniently prepared by methods well known to those skilled in the art. The preferred method of preparation involves condensing an appropriately substituted naphthalene derivative with a 2,4-dinitro-6-(trifluoromethyl)-1-(substituted)benzene derivative in the presence of a base to give a compound of the invention. The scheme for this reaction is as follows:

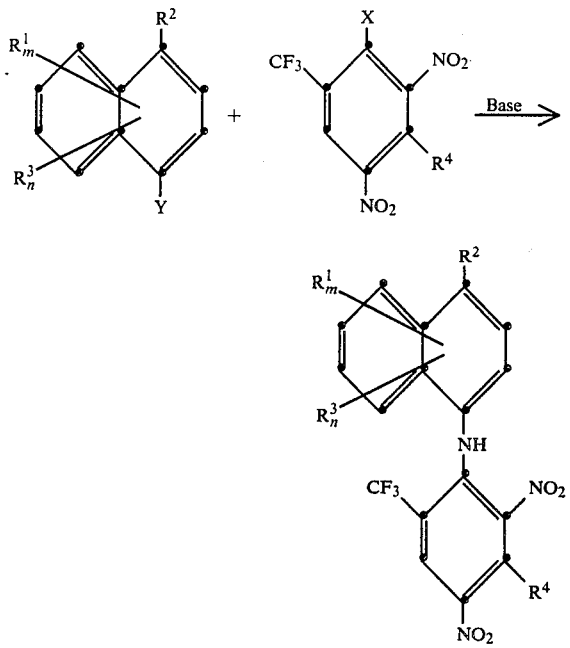

wherein $R^1$, $R^2$, $R^3$, $R^4$, m and n are as defined above, and one of X and Y is $NH_2$ and the other is a good leaving group such as halogen.

An example of this reaction scheme involves reacting a 1-naphthalenamine derivative with a halobenzene derivative. This reaction is generally performed by combining approximately equimolar quantities of the naphthalenamine and substituted halobenzene derivatives with at least one equivalent of base in a suitable organic solvent. Suitable solvents should be unreactive and include most aprotic solvents. Commonly used solvents include amides, for instance, N,N-dimethylformamide or hexamethylphosphoramide; ethers, such as tetrahydrofuran, diethyl ether and dioxane; sulfoxides, such as dimethyl sulfoxide; and related solvents. Of these, DMF is preferred.

The reaction is usually performed at a temperature in the range of from about −25° C. to 100° C., with 0° C. to 50° C. being preferred. The base used as a reactant should preferably be of sufficient strength to pull the nitrogen proton of the naphthalenamine derivative. Suitable bases include most of the alkali metal hydrides, for example sodium hydride and lithium hydride. Sodium hydride is preferred. Following formation of the product, which usually occurs after about 10 minutes to about 48 hours, the mixture is worked up according to standard procedures. Typically, the product may be isolated by simply adding to the reaction mixture either water or an aqueous acid solution, for instance dilute aqueous hydrochloric acid or sulfuric acid. The desired product often precipitates out of the aqueous acid solution as a solid or an oil and may be collected by filtration. Alternatively, the product may be extracted into a water immiscible organic solvent such as diethyl ether, ethyl acetate, dichloromethane, or the like. Removal of the organic solvent, for instance by evaporation under reduced pressure, then provides a compound of this invention. The product thus formed can be further purified if desired by any of several methods well known to those skilled in the art, for example by column chromatography over silica gel or crystallization from common solvents.

The following detailed examples are provided in an effort to more fully illustrate specific aspects of this invention. The examples are not intended to be limiting in any respect and should not be so construed.

EXAMPLE 1

4-Chloro-N-[2,4-dinitro-6-(trifluoromethyl)phenyl]-1-naphthalenamine

Two grams of sodium hydride were slowly added to a stirring solution of 3.5 g. of 4-chloro-1-naphthalenamine and 5.4 g. of 2,4-dinitro-6-(trifluoromethyl)-1-chlorobenzene dissolved in 30 ml. of DMF. The reaction mixture was stirred at room temperature for approximately 24 hours and poured into water. The precipitated solid was collected by filtration and recrystallized from ethanol to afford 4.7 g. of 4-chloro-N-[2,4-dinitro-6-(trifluoromethyl)phenyl]-1-naphthalenamine. Yield 57%.

M.P.=197°–198° C.

Analysis calculated for $C_{17}H_9ClF_3N_3O_4$,
Theory: C, 49.59; H, 2.20; N, 10.21;
Found: C, 49.31; H, 2.10; N, 10.07.

EXAMPLE 2

4-Bromo-N-[2,4-dinitro-6-(trifluoromethyl)phenyl]-1-naphthalenamime

A mixture of 4.4 g. of 4-bromo-1-naphthalenamine, 40 ml. of DMF and 2.0 g. of sodium hydride was slurried at room temperature for about 15 minutes. Next, 5.4 g. of 2,4-dinitro-6-(trifluoromethyl)-1-chlorobenzene was added to the reaction mixture in small portions. When the addition was completed, the mixture was allowed to stir at room temperature for about 24 hours. The mixture was then slowly added to a stirring solution of ice water and hydrochloric acid. The precipitated solid was collected by filtration and dried. The solid was recrystallized from ethanol/DMF, and collected by filtration to afford 2.1 g. of 4-bromo-N-[2,4-dinitro-6-(trifluoromethyl)phenyl]-1-naphthalenamine. Yield 23%.

M.P.=219°–221° C.

Analysis calculated for $C_{17}H_9BrF_3N_3O_4$,
Theory: C, 44.74; H, 1.97; N, 9.21;
Found: C, 45.35; H, 1.70; N, 9.33.

As noted above, the compounds of the present invention are preferably used in combination with a polyether antibiotic. The polyether antibiotics are a class of compounds produced by the Streptomyces genus of microorganisms. They are characterized by comprising a multiplicity of cyclic ethers in their structure. The class of compounds is reviewed in Kirk-Othmer: *Encyclopedia of Chemical Technology*, Vol. 3, Third Edition (John Wiley & Sons, Ind. 1978), page 47 et seq.; in *Annual Reports in Medicinal Chemistry*, Vol. 10, (Academic Press, N.Y. 1975), page 246 et seq.; and in *J. Chrom. Lib.*, Vol. 15 (Elsevier Scientific Publishing Co., N.Y., 1978), page 488 et seq.

As with most products of fermentation, the polyether antibiotics generally comprise more than one factor. The combinations provided as one aspect of this invention include the various individual factors as well as mixtures thereof. Also, many of the polyether antibiotics form derivatives such as esters, ethers, salts, amides, or the like, and these generally are active themselves or are readily converted in vivo to an active form of the antibiotic. Accordingly, all such derivatives are usable in combinations of this invention. All that is necessary is that an active moiety of a polyether antibiotic be delivered in vivo so as to reach the site of coccidial infection.

Typical of the polyether antibiotics to be employed in the combinations of this invention are the following. Monensin, which includes principal factors A, B and C and salts thereof, is described in U.S. Pat. No. 3,501,568. Several derivatives of monensin have been disclosed, for instance in U.S. Pat. No. 3,832,358 and European Pat. No. 11,859. A particularly preferred combination of this invention is monensin, primarily factors A and B, as the sodium salt, together with a compound of the invention. Also preferred is the combination of the 4-bromophenylurethan of monensin described in EP No. 11,859, together with a present novel compound.

Polyether antibiotics, A204, lasalocid (X-537A), dianemycin, nigericin and X-206 are described in U.S. Pat. No. 3,794,732. A number of derivatives of lasalocid are described in U.S. Pat. Nos. 3,944,573 and 4,247,690.

Ionomycin is a polyether antibiotic obtained by cultivating the microorganism *Streptomyces conglobatus* ATCC No. 31005. The production of ionomycin and its properties are described in U.S. Pat. No. 3,873,693.

Laidlomycin is a polyether antibiotic described by Kitame et al. in *J. Antibiot.*, 27, 884–888 (1974).

Grisorixin is the name assigned to deoxynigericin, and is described in French Pat. No. 2,097,053. As noted above, nigericin is disclosed in U.S. Pat. no. 3,794,732.

Lenoremycin, also referred to as "antibiotic A-130A", is a polyether antibiotic produced by *Streptomyces hydroscopicus* ATCC No. 21840. The properties of lenoremycin are detailed in U.S. Pat. No. 3,903,264.

U.S. Pat. Nos. 4,038,384 and 4,085,224 describe the preparation and use of narasin and salinomycin. Narasin is referred to therein as "A-28086".

Lonomycin is a polyether also known as "antibiotic TM481", "antibiotic DE 3936" and "emericid". Its preparation and use are described in *J. Antibiotics*, 29, No. 1, 15–20 (1976). Derivatives of lonomycin are disclosed in U.S. Pat. No. 4,199,515.

Alborixin, also known as "S14750/A" is derived from *Streptomyces hygroscopicus* NRRL 5077 and is described in British Pat. No. 1,541,485.

Septamycin is a polyether produced by cultivating *Streptomyces albus* NRRL 3883. This compound was initially referred to as "A28695A" and "A28695B", as well as "BL580". Its properties are described in U.S. Pat. Nos. 3,839,558 and 4,189,537.

Etheromycin is also known as "antibiotic 38295" and "CP38295". It is disclosed in U.S. Pat. No. 4,129,578.

Mutalamycin is a polyether derivative of lonomycin and is described in Belgian Pat. No. 845,708. It is also referred to as "S11743A".

Preferred polyether antibiotics to be employed in the combinations of this invention include monensin, monensin phenylurethan derivatives, narasin, lasalocid, salinomycin, A-204, lonomycin, X-206, nigericin, and dianemycin.

The term "effective anticoccidial amount", as defined herein refers to an amount of a compound or combination of the invention which kills or severely inhibits the growth of coccidiosis disease causing organisms. When a compound of the invention is used alone as a coccidiostat, this amount will generally be from about 1 to about 1000 ppm, more preferably from about 10 to 400 ppm of naphthalenamine. The exact concentration of compound required depends on the organism sought to be controlled, animal type, and the organism sought to be controlled, animal type, and the like. The anticoccidial amounts required for combinations of the invention are detailed below.

According to another aspect of this invention, a polyether antibiotic and a compound disclosed herein are employed for the control of coccidiosis in combination, in amounts of about 1 to about 10 parts by weight of polyether antibiotic and about 10 to about 1 part by weight of a compound of the invention. The invention will typically be practiced in treating coccidiosis in poultry, and the treatment is generally accomplished by orally administering to the poultry to be treated a poultry feedstuff comprising an amount of the naphthalenamine, and an amount of a polyether antibiotic which in combination are effective against at least one coccidiosis-causing strain of Eimeria. Typically, a present naphthalenamine will be employed in the combination in an amount from about 10 to about 400 ppm. Exemplary amounts of typical polyether antibiotics to be employed are:

from about 20 to about 120 ppm of monensin;
from about 25 to about 100 ppm of narasin;
from about 35 to about 125 ppm of lasalocid;
from about 25 to about 100 ppm of salinomycin
from about 1 to about 50 ppm of A-204;
from about 50 to about 100 ppm of dianemycin;
from about 40 to about 80 ppm of ionomycin;
from about 10 to about 120 ppm of monensin factor A or 4-nitrophenylurethan;
from about 30 to about 200 ppm of laidlomycin;
from about 15 to about 95 ppm of grisorixin;
from about 20 to about 95 ppm of lenoremycin;
from about 15 to about 150 ppm of mutalomycin;
from about 50 to about 200 ppm of nigericin;
from about 10 to about 120 ppm of X-206.

While a preferred embodiment of the invention is a combination wherein a single polyether antibiotic and a compound of the invention are the sole anticoccidial agents, a combination can contain more than one polyether antibiotic and more than one novel compound. For example, a combination of the invention may comprise about 1 part by weight of a naphthalenamine, about 5 parts by weight of lasalocid, and about 5 parts by weight of salinomycin. The most preferred combination of the invention is, however, about 1 to 2 parts by weight of naphthalenamine and from about 1 to about 10 parts by weight of monensin, especially monensin factors A and B as the sodium salts. A particularly preferred composition for feeding to poultry according to this invention is one containing from about 5 to about 50 ppm of a naphthalenamine and from about 25 to about 80 ppm of commercially available monensin. The most preferred compound of the invention to be employed in the combinations of this invention is 4-bromo-N-[2,4-dinitro-6-(trifluoromethyl)phenyl]-1-naphthalenamine.

As noted above, preferred methods of the invention comprise treating poultry for coccidial infections. The compounds and compositions of the present invention can be used with all species of poultry, for example quail, ducks, geese, pheasants, chickens and turkeys. Because of their economic importance, chickens and turkeys are the typical recipients of anticoccidial treatment. Typical poultry coccidiosis causing organisms which the present compounds and combinations are useful in eradicating include *Eimeria necatrix, E. tenella, E. acervulina, E. brunetti, E. mivati,* and *E maxima.*

The methods provided herein may be practiced for the prophylactic control of coccidiosis, for instance by the routine and continued administration to an animal susceptible to coccidiosis of an effective amount of a compound or combination provided by the invention, as well as for the therapeutic treatment of coccidiosis in animals so infected. The compounds and combinations can be formulated for convenient administration to animals by any number of routes, including the oral, intramuscular, intravenous, subcutaneous and related routes. The compounds and combinations are preferably formulated for systemic administration to animals.

For treatment of poultry according to this invention, the naphthalenamines, both alone and in combination with polyether antibiotics, are preferably formulated for oral administration, for instance as a feedstuff, by addition to the normal daily feed ration of the animals. Ideally, the compound or combination will be uniformly dispersed throughout a finished animal feed mixture. Such medicated feed mixture is then administered ad lib. to animals such as chickens and turkeys. The normal concentration of compound or combination to be employed in a feedstuff will be from about 10 grams per ton to about 400 grams per ton, and more preferably about 20 g/T to about 200 g/T. Poultry will routinely consume about 5 to about 200 grams of such feedstuff per day, depending upon size and age of the bird.

Any of a number of poultry feedstuffs can be utilized as suitable carriers or diluents for the compounds or combinations defined above. Typical feedstuffs include the following:

| Ingredients | Percent |
|---|---|
| Broiler Starter | |
| Corn, Yellow, Ground | 50.0 |
| Soybean Oil Meal, Solvent Extracted, Dehulled (50%) | 30.9 |
| Animal Fat | 6.5 |
| Fish Meal with Solubles (60%) | 5.0 |
| Corn Distillers Dried Solubles | 4.0 |
| Dicalcium Phosphate, Feed Grade | 1.8 |
| Calcium Carbonate (Ground Limestone) | 0.8 |
| Vitamin Premix TK-1 (1.03)[1] | 0.5 |
| Salt (NaCl) | 0.3 |
| Trace Mineral Premix TK-01 (1.02)[2] | 0.1 |
| Methionine Hydroxy Analog | 0.1 |
| Total | 100.0 |
| Broiler Grower | |
| Corn, Yellow, Ground | 57.7 |
| Soybean Meal, Solvent, Extracted, Dehulled (50%) | 31.7 |
| Animal Fat (Beef tallow) | 6.0 |
| Dicalcium Phosphate, Feed Guide | 2.7 |
| Calcium Carbonate (Ground Limestone) | 0.9 |
| Vitamin Premix TK-01 (1.03)[1] | 0.5 |
| Salt (NaCl) | 0.2 |
| Methionine Hydroxy Analog | 0.2 |
| Trace Mineral Premix TK-01 (1.02)[2] | 0.1 |
| Total | 100.0 |
| Chick Starter, Light Breeds | |
| Corn, Yellow, Ground | 56.3 |
| Soybean Meal, Solvent Extracted, Dehulled (50%) | 17.9 |
| Wheat Middlings | 10.0 |
| Corn Distillers Dried Solubles | 5.0 |
| Fish Meal with Solubles | 5.0 |
| Alfalfa Meal, Dehydrated (17%) | 2.5 |
| Dicalcium Phosphate, Feed Grade | 1.3 |
| Calcium Carbonate | 0.9 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Grower | |
| Corn, Yellow, Ground | 73.5 |
| Soybean Meal, Solvent Extracted, Dehulled (50%) | 21.9 |
| Dicalcium Phosphate, Feed Grade | 2.5 |
| Calcium Carbonate | 1.0 |
| Vitamin Premix[1] | 0.5 |
| Salt (NaCl) | 0.3 |
| Methionine Hydroxy Analog | 0.2 |
| Trace Mineral Premix[2] | 0.1 |
| Total | 100.0 |
| Pullet Developer | |
| Corn, Yellow, Ground | 67.5 |
| Oats, Ground Whole | 15.0 |
| Soybean Meal, Solvent Extracted, Dehulled (50%) | 13.4 |
| Dicalcium Phosphate, Feed Grade | 2.1 |
| Calcium Carbonate | 1.0 |
| Vitamin Premix[1] | 0.5 |
| Methionine Hydroxy Analog | 0.3 |
| Salt (NaCl) | 0.2 |
| Trace Mineral Premix[2] | 0.1 |
| Total | 100.0 |
| Turkey Starter | |
| Soybean Meal, Solvent Extracted, Dehulled | 40.7 |
| Corn, Yellow, Ground | 39.7 |
| Fish Meal with Solubles | 5.0 |
| Beef Tallow | 5.0 |
| Corn Distillers Dried Solubles | 2.5 |
| Alfalfa Meal, Dehydrated (17%) | 2.5 |
| Dicalcium Phosphate, Feed Grade | 2.5 |
| Calcium Carbonate | 1.2 |
| Vitamin Premix[1] | 0.5 |
| Salt (NaCl) | 0.2 |
| Trace Mineral Premix[2] | 0.1 |
| Methionine Hydroxy Analog | 0.1 |
| Total | 100.0 |
| Turkey Finisher | |
| Corn, Yellow, Ground | 71.2 |
| Soybean Meal, Solvent Extracted, Dehulled (50%) | 9.9 |
| Corn Distillers Dried Solubles | 5.0 |
| Alfalfa Meal, Dehydrated (17%) | 5.0 |
| Animal Fat | 3.0 |
| Fish Meal with Solubles | 2.5 |
| Dicalcium Phosphate, Feed Grade | 1.7 |
| Calcium Carbonate | 0.5 |
| Vitamin Premix[1] | 0.5 |
| Salt (NaCl) | 0.4 |
| Methionine Hydroxy Analog | 0.2 |
| Trace Mineral Premix[2] | 0.1 |
| Total | 100.0 |

[1]Vitamin premix provides 3000 IU of vitamin A, 900 ICU of vitamin D, 40 mg. of vitamin E., 0.7 mg. of vitamin K, 1000 mg. of choline, 70 mg. of niacin, 4 mg. of pantothenic acid, 4 mg. of riboflavin, 0.10 mg. of vitamin $B_{12}$, 0.10 mg. of biotin and 125 mg. of ethoxyquin per kg. of complete feed.
[2]Trace mineral premix provides 75 mg. of manganese, 50 mg. of zinc, 25 mg. of iron and 1 mg. of iodine per kg. of complete feed.

A compound of the present invention can be admixed with any such poultry feedstuffs so that the final feedstuff contains from about 10 to about 400 grams of naphthalenamide per ton of feedstuff. For example, about 100 g. of 4-(3,3,3-trifluoropropyl)-N-[2,4-dinitro-6-(trifluoromethyl)phenyl]-1-naphthalenamine can be added to about one ton of Broiler Grower mixture to provide a suitable formulation. Similarly, about 200 g. of 4-fluoro-N-[3-chloro-2,4-dinitro-6-(trifluoromethyl)-phenyl]-1-naphthalenamine can be uniformly admixed with about one ton of Turkey Finisher for administration to turkeys.

Similarly, an anticoccidial combination of the invention can be admixed with any such poultry feedstuff so that the final feedstuff contains about 10 to about 400 grams of active agent per ton of feedstuff. For example, about 50 g. of 4-bromo-N-[2,4-dinitro-6-trifluoromethyl)phenyl]-1-naphthalenamine can be added to about 50 g of monensin sodium and combined with about one ton of Broiler Grower mixture as prepared above for use according to this invention. Also, about 60 g. of a naphthalenamine of the invention can be combined with about 60 g. of a monensin urethane derivative and combined with about one ton of Turkey Finisher for administration to turkeys pursuant to the present method.

The compounds and combinations of the present invention can also be formulated as a feedstuff premix by mixing either with a suitable physiologically-acceptable carrier or diluent. Examples of such carriers or diluents include rice hulls, ground corn cobs, and finely divided material derived from cereal grains; oil seeds and their byproducts; forages, silages, and their by-products; by-products of the lumber, sugar, fruit juice, and vegetable juice industries; clays such as diatomaceous earth; vermiculite; solvent-extracted soybean feed; soybean mill run; corn flour; milo flour; wheat middlings; and alfalfa meal. A mixture of a present compound and carrier or diluent will preferably contain about 5 to about 90 percent by weight of the naphthalenamine, and more preferably about 20 to about 70 percent by weight. This premix formulation is then usually mixed with a normal feed ration at a rate so that the active ingredient is present in about 10 to about 400 grams per ton of final feed ration.

A compound or combination of the invention substantially dissolved in water, for example in the drinking water of poultry such as chickens and turkeys, comprises yet another formulation provided by this invention. Due to the low solubility typical of the present compounds in water, it is preferable to prepare water-soluble powders or dispersible powders comprising a compound of the invention admixed with carriers such as dextrose, sucrose, dimethyl sulfoxide, or the like. Typically, the naphthalenamine will be present in such forms in about 0.01 to about 30 percent by weight. Such powder or liquid formulations are conveniently added to the poultry drinking water at the site of administration.

The anticoccidial activity of representative compounds and combinations of the present invention is demonstrated by the following experiments.

EXPERIMENT 1

The compounds provided by this invention display anticoccidial activity. The initial screen used to determine such activity in vivo was performed as follows. Five one-week-old broiler chicks were placed in the same cage. The animals were fed a medicated or control ration for one day prior to infection with oocysts of the coccidiosis-causing organism *Eimeria tenella*. The chicks were maintained on their respective rations for a period of time after infection, typically for seven days. Anticoccidial efficacy was then determined by cecal lesion scores. In determining lesion scores, the birds were sacrificed and the severity of lesions were scored on a 0-4 scale, with lesion free birds scored as 0, extremely severe infections scored as 4, and intermediate degrees of infection scored as 1, 2, or 3. The scores of all birds which received a given treatment were averaged.

Table 1 which follows presents the results of tests performed with Examples 1 and 2 of the present invention. It is also indicated in the Table in the event the concentration of the test compound administered to the birds was toxic.

TABLE 1

| Example No. of Compound Tested | Concentration (ppm) | Cecal Lesion Score |
| --- | --- | --- |
| 1 | 200 | 0.0 (toxic) |
| 2 | 200 | 0.0 (toxic) |
|   | 190 | toxic |
|   | 47 | 4.0 |

EXPERIMENT 2

Examples 1 and 2 of the present invention were also tested against additional coccidiosis-causing organisms and at lower concentrations of test compound. This experiment was performed in the same manner as Experiment 1 with the exception that the birds were fed the medicated or control ration for two days prior to infection. The additional organisms tested against were *Eimeria acervulina* and *Eimeria maxima*, which act in the intestine of the birds. The scores were also recorded as above with the exception that intestinal lesions were scored in three areas of the gut so that the total theoretical lesions for the intestinal score is 12. The animals were inoculated with strains of *Eimeria acervulina* (strain 59) and *Eimeria maxima* (strain F.S. 177). Tables 2 and 3 present the results of these tests.

TABLE 2

| Treatment | Dose (ppm) | Intestinal Lesion Scores | |
| --- | --- | --- | --- |
|  |  | Replicates | Mean |
| Control |  | 2 | 5.10 |
| Example 1 | 50 | 3 | 0.00 |
|  | 25 | 3 | 0.07 |
|  | 10 | 3 | 3.93 |
|  | 5 | 3 | 6.47 |

TABLE 3

| Treatment | Dose (ppm) | Intestinal Lesion Scores | |
| --- | --- | --- | --- |
|  |  | Replicates | Mean |
| Control |  | 3 | 4.93 |
| Example 2 | 100 | 3 | 0.00 |
|  | 50 | 3 | 0.00 |
|  | 30 | 3 | 0.40 |
|  | 20 | 3 | 0.20 |
|  | 10 | 3 | 5.73 |

Intestinal and cecal lesion scores were assigned to broiler cockerels inoculated with *Eimeria acervulina* (strain 59), *Eimeria tenella* (strain 155), and *Eimeria maxima* (strain F.S. 177). The results of these experiments appear in Tables 4-7 below.

TABLE 4

| Treatment | Dose (ppm) | Lesion Scores | | | |
| --- | --- | --- | --- | --- | --- |
|  |  | Intestinal | | Cecal | |
|  |  | Replicates | Mean | Replicates | Mean |
| Control |  | 3 | 6.40 | 3 | 2.73 |
| Example 1 | 200 | 3 | 0.00 | 3 | 1.56 |
|  | 175 | 3 | 0.00 | 3 | 0.30 |
|  | 150 | 3 | 0.00 | 3 | 0.33 |

TABLE 5

| Treatment | Dose (ppm) | Lesion Scores Intestinal Replicates | Mean | Cecal Replicates | Mean |
|---|---|---|---|---|---|
| Control |  | 3 | 1.5 | 3 | 3.44 |
| Example 1 | 150 | 2 | 0.00 | 2 | 1.50 |
|  | 100 | 2 | 0.00 | 2 | 0.96 |
|  | 50 | 2 | 0.00 | 2 | 1.20 |

TABLE 6

| Treatment | Dose (ppm) | Lesion Scores Intestinaal Replicates | Mean | Cecal Replicates | Mean |
|---|---|---|---|---|---|
| Control |  | 2 | 4.40 | 2 | 3.20 |
| Example 2 | 200 | 3 | 0.00 | 3 | 0.93 |
|  | 150 | 3 | 0.00 | 3 | 0.00 |
|  | 100 | 3 | 0.00 | 3 | 0.87 |

TABLE 7

| Treatment | Dose (ppm) | Lesion Scores Intestinal Replicates | Mean | Cecal Replicates | Mean |
|---|---|---|---|---|---|
| Control |  | 2 | 4.53 | 2 | 3.90 |
| Example 2 | 40 | 3 | 0.33 | 3 | 2.80 |
|  | 20 | 2 | 3.30 | 2 | 3.70 |
|  | 10 | 2 | 4.63 | 2 | 3.75 |

Example 2 of the present invention was also tested in combination with monensin according to the procedure of Experiment 2. The results of these tests appear below in Tables 8–11.

TABLE 8

Intestinal Lesion Scores

| Example 2 (ppm) | Monensin (ppm) 0 | 25 | 50 | 100 |
|---|---|---|---|---|
| 0 | 4.53 | 1.50 | 1.30 | 0.00 |
| 10 | 4.63 | 0.60 | 0.00 | 0.00 |
| 20 | 3.30 | 0.00 | 0.00 |  |
| 40 | 0.33 |  |  |  |

TABLE 9

Cecal Lesion Scores

| Example 2 (ppm) | Monensin (ppm) 0 | 25 | 50 | 100 |
|---|---|---|---|---|
| 0 | 3.90 | 3.33 | 2.10 | 0.00 |
| 10 | 3.75 | 2.73 | 1.27 |  |
| 20 | 3.70 | 1.07 | 0.80 |  |
| 40 | 2.80 |  |  |  |

The combinations herein provided also cause a beneficial effect on weight gain of animals. For example, poultry receiving the combinations gain more weight than when receiving the individual ingredients, and also exhibit a better feed to gain ratio. The following data demonstrates the improved weight gain and feed utilization efficiency of broiler cockerals when receiving a combination of monensin sodium salt and Example 2.

TABLE 10

Average Survivor Weight Gain in Grams

| Example 2 (ppm) | Monensin (ppm) 0 | 25 | 50 | 100 |
|---|---|---|---|---|
| 0 | 169.1 | 167.0 | 244.1 | 219.1 |
| 10 | 157.1 | 216.7 | 244.1 |  |
| 20 | 181.4 | 230.2 | 235.3 |  |

TABLE 10-continued

Average Survivor Weight Gain in Grams

| Example 2 (ppm) | Monensin (ppm) 0 | 25 | 50 | 100 |
|---|---|---|---|---|
| 40 | 181.9 |  |  |  |

TABLE 11

Average Feed/Gain

| Example 2 (ppm) | Monensin (ppm) 0 | 25 | 50 | 100 |
|---|---|---|---|---|
| 0 | 2.542 |  | 1.525 | 1.604 |
| 10 |  | 1.621 | 1.535 |  |
| 20 | 1.847 | 1.611 | 1.574 |  |
| 40 | 1.834 |  |  |  |

We claim:

1. A compound of the formula wherein:
$R^2$ is halogen;
$R^4$ is hydrogen;
m is 0; and
n is 0.

2. The compound of claim 1 which is 4-chloro-N-[2,4-dinitro-6-(trifluoromethyl)phenyl]-1-naphthalenamine.

3. The compound of claim 1 which is 4-bromo-N-[2,4-dinitro-6-(trifluoromethyl)phenyl]-1-naphthalenamine.

4. A composition comprising a carrier or diluent and an effective anticoccidial amount of a compound of claim 1.

5. The composition of claim 4 wherein the carrier is a poultry feedstuff.

6. The composition of claim 4 wherein the carrier is a poultry premix.

7. The composition of claim 4 wherein the compound is 4-chloro-N-[2,4-dinitro-6-(trifluoromethyl)phenyl]-1-naphthalenamine.

8. The composition of claim 4 wherein the compound is 4-bromo-N-[2,4-dinitro-6-(trifluoromethyl)phenyl]-1-naphthalenamine.

9. A combination useful in the treatment of coccidiosis in animals comprising an effective anticoccidial amount of a polyether antibiotic and a compound of claim 1.

10. The combination of claim 9 wherein the polyether antibiotic is selected from the group consisting of monensin, monensin phenylurethane derivatives, A204, lasalocid, dianemycin, nigericin, X-206, ionomycin, laidlomycin, grisorixin, lenoremycin, narasin, salinomycin, lonomycin, alborixin, septamycin, etheromycin and mutalamycin.

11. The combination according to claim 10 wherein the polyether antibiotic employed is selected from the group consisting of monensin, monensin 4-bromophenylurethan, narasin, lasalocid, salinomycin, A-204, lonomycin, X-206, nigericin and dianemycin.

12. The combination of claim 11 wherein the polyether antibiotic is monensin.

13. The combination of claim 11 wherein the polyether antibiotic is narasin.

14. The combination of claim 11 wherein the polyether antibiotic is lasalocid.

15. The combination of claim 11 wherein the polyether antibiotic is monensin 4-bromophenylurethan.

16. The combination of claim 9 wherein the compound is 4-bromo-N-[2,4-dinitro-6-(trifluoromethyl)phenyl]-1-naphthalenamine.

17. The combination of claim 16 wherein the polyether antibiotic is monensin.

18. The combination of claim 9 wherein the compound is 4-chloro-N-[2,4-dinitro-6-(trifluoromethyl)phenyl]-1-naphthalenamine.

19. A composition comprising an effective anticoccidial amount of a combination of claim 9 and a suitable carrier or diluent.

20. The composition of claim 19 wherein the carrier is a poultry feedstuff.

21. The composition of claim 19 wherein the carrier is a poultry premix.

22. The composition of claim 21 wherein the combination comprises monensin and 4-bromo-N-[2,4-dinitro-6-(trifluoromethyl)phenyl]-1-naphthalenamine.

23. A method for controlling coccidiosis in animals comprising administering to an animal an effective anticoccidial amount of a combination of claim 9.

24. A method of claim 23 wherein the animals treated are poultry and the route of administration is oral.

25. The method of claim 24 wherein the combination employed comprises monensin.

26. The method of claim 24 wherein the combination employed comprises 4-bromo-[2,4-dinitro-6-(trifluoromethyl)phenyl]-1-naphthalenamine.

* * * * *